United States Patent

Michaels et al.

[11] Patent Number: 5,906,672
[45] Date of Patent: *May 25, 1999

[54] CLOSED-LOOP FEEDBACK CONTROL FOR OXYGEN CONCENTRATOR

[75] Inventors: Gregory A. Michaels, Seven Hills; Homayoun Birangi, Willoughby; David D. Polaseck, Elyria, all of Ohio

[73] Assignee: Invacare Corporation, Elyria, Ohio

[21] Appl. No.: 08/873,391

[22] Filed: Jun. 12, 1997

Related U.S. Application Data

[60] Provisional application No. 60/019,908, Jun. 14, 1996.

[51] Int. Cl.$^6$ .................................................. B01D 53/047
[52] U.S. Cl. ................... 95/12; 95/21; 95/96; 95/130; 96/111; 96/113; 96/130; 96/144
[58] Field of Search ............... 95/8, 11, 12, 19, 95/21, 96–105, 130; 96/111, 113–115, 117, 130, 144

[56] References Cited

U.S. PATENT DOCUMENTS

| | | | |
|---|---|---|---|
| 2,944,627 | 7/1960 | Skarstrom | 95/26 |
| 3,142,547 | 7/1964 | Marsh et al. | 95/100 |
| 3,280,536 | 10/1966 | Berlin | 95/130 X |
| 3,313,091 | 4/1967 | Berlin | 95/130 X |
| 4,222,750 | 9/1980 | Gauthier et al. | 95/130 X |
| 4,247,311 | 1/1981 | Seibert et al. | 96/111 |
| 4,259,548 | 3/1981 | Fahey et al. | 179/5 R |
| 4,263,018 | 4/1981 | McCombs et al. | 95/19 |
| 4,336,590 | 6/1982 | Jacq et al. | 364/418 |
| 4,449,990 | 5/1984 | Tedford, Jr. | 95/26 |
| 4,459,266 | 7/1984 | Lamoreaux | 422/86 |
| 4,472,177 | 9/1984 | Sircar | 95/19 X |
| 4,516,424 | 5/1985 | Rowland | 73/23 |
| 4,561,287 | 12/1985 | Rowland | 73/23 |
| 4,576,616 | 3/1986 | Mottram et al. | 95/130 X |
| 4,627,860 | 12/1986 | Rowland | 96/111 |
| 4,648,888 | 3/1987 | Rowland | 55/21 |
| 4,687,013 | 8/1987 | Stevenson | 96/111 X |
| 4,822,384 | 4/1989 | Kato et al. | 96/111 X |
| 4,857,086 | 8/1989 | Kawai et al. | 96/111 |
| 5,071,453 | 12/1991 | Hradek et al. | 95/19 X |
| 5,247,826 | 9/1993 | Frola et al. | 73/24.01 |
| 5,340,381 | 8/1994 | Vorih | 95/21 |
| 5,407,465 | 4/1995 | Schaub et al. | 95/130 X |
| 5,469,372 | 11/1995 | McBrearty et al. | 364/550 |
| 5,474,595 | 12/1995 | McCombs | 95/130 X |
| 5,486,226 | 1/1996 | Ross et al. | 96/111 X |
| 5,490,871 | 2/1996 | Coates et al. | 95/130 X |
| 5,529,607 | 6/1996 | Tan | 95/12 |
| 5,531,807 | 7/1996 | McCombs | 95/130 X |
| 5,593,478 | 1/1997 | Hill et al. | 96/111 |
| 5,627,323 | 5/1997 | Stern | 73/861.28 |

FOREIGN PATENT DOCUMENTS

| | | |
|---|---|---|
| 0 732 137 A2 | 1/1996 | European Pat. Off. . |
| 296 05 889 U1 | 8/1996 | Germany . |
| 63-307101 | 12/1988 | Japan ......... 95/12 |
| 2-307507 | 12/1990 | Japan ......... 96/111 |
| 3-021317 | 1/1991 | Japan ......... 96/111 |
| 4-187210 | 7/1992 | Japan ......... 96/111 |

*Primary Examiner*—Robert H. Spitzer
*Attorney, Agent, or Firm*—Hudak & Shunk Co., L.P.A.

[57] ABSTRACT

An oxygen concentrator is provided which has a first molecular sieve bed connected to a four-way valve (i.e., a cross-over valve) which either joins the sieve bed to a pressurized air source (compressed air) or alternatively vents it to atmosphere. A second molecular sieve bed is also joined to the four-way valve in a corresponding manner. The sieve beds are joined at the outlet end to a product reservoir. The sieve beds are also in fluid communication at the outlet end by a pressure equalization flow path. A concentration equalization valve regulates the flow in the pressure equalization flow path. In accordance with the present invention, the microprocessor uses a closed-loop feedback circuit to evaluate the amount of time that the output product gas is allowed to flow into the used sieve bed. Specifically, an incremental step advance is used assuming a peak value of the time of flow one direction as compared to the time of flow in the second direction. Thus, so long as the measured oxygen output to the patient keeps increasing, the control will direct incremental advances in the valve setting in the same direction. When the measured value decreases, the control steps back to the previous setting (i.e., the penultimate setting). In a second embodiment, control is based on a variable residence time range and variable pressure set point.

25 Claims, 4 Drawing Sheets

CLOSED-LOOP FEEDBACK CONTROL FOR OXYGEN CONCENTRATOR

CROSS-REFERENCE

The present application claims priority to U.S. Provisional patent application Ser. No. 60/019,908, filed Jun. 14, 1996, entitled "Closed-Loop Feed Control for Oxygen Concentrator."

FIELD OF INVENTION

The present invention relates to fractionating gases and more specifically to a control system for regulating the relative flow between molecular sieve beds in order to maximize the oxygen output from an oxygen concentrator to the user.

BACKGROUND OF THE INVENTION

Various applications exist for the separation of gaseous mixtures, and in particular for the separation of nitrogen from atmospheric air to provide a source of highly concentrated oxygen. These applications include the provision of elevated concentrations of oxygen for (1) patients requiring the same in their breathing air and (2) flight personnel. Additional applications relate to processes such as drying high-purity gases such as separating hydrogen from hydrocarbons.

U.S. Pat. No. 2,944,627, issued Jul. 12, 1960, to Charles Skarstrom illustrates an early apparatus and method for fractionating gases having first and second fractionating vessels packed with molecular sieve material which selectively adsorbed one or more components of the gas so as to pass through an enriched product gas. A cross-over valving assembly allowed for a flow correspondence between the vessels and with a waste gas discharge. Product gas from a vessel was channeled to a primary product outlet with a large fraction being channeled to the other vessel. This fraction flushed the adsorbed or waste gases which had been trapped by the other vessel. The cross-over valve assembly cyclically switched the connection of the vessels with the incoming gas and the waste gas discharge. This cyclic switching of the vessels provided a regular flow of the primary product gas from the primary product outlet.

U.S. Pat. No. 3,313,091, to Berlin, improved upon the Skarstrom system through the utilization of a vacuum pump to draw adsorbed or waste gases from the vessel or bed being purged. Additionally this invention utilized a more complex valving system to produce a cycle which included vessel or bed pressure equalization, repressurization product production, bed pressure equalization, dumping, and purging.

U.S. Pat. No. 4,222,750, to Gauthier et al. related to a specifically defined timing cycle in which primary product gas from the adsorbing bed was passed through the desorbing bed during the desorption cycle. The vessels were connected to a compressor during a period of adsorption and to a vacuum pump during a period of desorption.

U.S. Pat. No. 4,449,990, to Tedford Jr. improved upon these prior art patents by teaching a method and apparatus for fractionating oxygen in which a pair of molecular sieve beds were cyclically connected in a timed cycle by a first cross-over valve (i.e., a four-way valve) with a source of pressurized air and a method of depressurizing the bed. The outlet ends of the beds were further connected by a flow path referred to as a pressure equalization flow path including a pressure equalization valve ("PE" valve) for selectively opening and closing the flow path. The path included two flow conduits including a limited conduit which is always open and a regulated flow conduit which has the PE valve for variable flow rate. Further in that patent, a timing and control circuit regulated the cross-over valve such that the pressure equalization valve was open 1 percent of the cycle duration before the cross-over valve reversed positions and was closed 2 percent of the cycle duration after the cross-over valve changed positions.

Generally in the prior art as represented by these and other patents, an equalization valve is disposed between a pair of check valves at the outlet ends of a pair of sieve beds in an oxygen concentrator system. While the equalization valve was referred to by Tedford as a pressure equalization valve (i.e., a "PE" valve), in this invention we will refer to the corresponding valve as a concentration equalization valve (i.e., a "CE" valve). Ultimately the same result is achieved of allowing a purge supply of product gas to enter a used bed; however, with a pressure-based supply, the rationale for using the valve varies slightly. Specifically the equalization valve acts to dampen the oscillation of the output gas concentration into the product tank which may otherwise occur. An oxygen concentration sensor measures and provides an indication of whether or not a certain oxygen level is met. For example, normal or acceptable operation may exhibit a green light at a reading of 85 percent or above; a yellow light may be illuminated at a reading between 73 and 85 percent; and a red light illuminates at a reading below 73 percent and the device subsequently powers down. This information is merely displayed to the patient or technician. That is, the technician manually controls the equalization valve in an effort to fine-tune the oxygen supply to the patient based on the indicator lights and oxygen readings.

In accordance with the present invention, the oxygen sensor communicates with the concentration equalization valve by means of the microprocessor which utilizes a closed-loop control to provide automated operation and optimization of oxygen levels from the sieve beds to the patient. In the prior art as represented by the '990 patent, the equalization valve is set manually. This valve provides for the cyclic flow of gas from the producing bed to the evacuated bed to provide sieve bed purge and to stabilize the oxygen content of the product gas passed into the product reservoir. Specifically, the valve settings change the time that the valve is open in one direction allowing purge gas (i.e., from one bed to the second) as compared to the time that the valve is open allowing flow in the second direction.

In the present invention, a closed-loop control circuit is provided to continuously and automatically regulate the setting of the concentration equalization valve. An oxygen sensor located between the reservoir or product tank and the patient, communicates information to the microprocessor which is programmed to evaluate the relative efficiencies of the sieve bed and thereby used to control operation of the concentration equalization valve.

Further in accordance with this invention, the operation of the oxygen concentrator is optimized through the use of information regarding the relative output flow rates between the sieve beds. The concentration equalization valve allows oxygen from the first sieve bed to mix with oxygen from the second sieve bed. The amount of time that gas is allowed to flow into the used sieve bed is determined by the concentration equalization valve adjustment. Closed-loop feedback with oxygen concentration provides the optimum setting for the concentration equalization valve (time allowed for balance of the first and second sieve beds). However, the optimum setting may change as a function of compressor flow output rate. This rate is dependent upon such things as altitude, compressor age, filter condition, and line voltage. By using a pressure transducer in the product tank, the pressure swing cycle can be controlled using electronic control means such as an integrated or remote microprocessor programmed with the appropriate software. The microprocessor is programmed to perform a step-wise adjustment in order to optimize the concentration equalization valve setting and consequently to optimize the oxygen concentration output.

The concentration equalization valve setting can be achieved initially by selecting the correct starting point. However, the relative efficiencies of the bed and the relative efficiencies of the corresponding concentration equalization valve setting of the beds may change during use. For example, after optimization at one extreme of the flow rate specification, a sudden change in flow rate may result in a concentration equalization valve setting inappropriate for the other extreme of the flow rate specification. The sudden change may cause the oxygen concentration to fall below the alarm threshold prior to achieving the new optimized concentration equalization valve setting causing the unit to shut down. By adjusting to a predetermined flow rate, the concentration equalization valve setting can be preprogrammed and the appropriate starting point also known. Therefore, the time required to achieve optimization is greatly reduced and further may be accomplished automatically, eliminating the need for an immediate service call by a technician.

SUMMARY OF THE INVENTION

In accordance with the present invention, there is provided a method of fractionating components of a gaseous mixture. Concurrently, the gaseous mixture is supplied under pressure to a bed of a physical separation medium which adsorbs at least one adsorbable component and passes at least one substantially nonadsorbable component of the mixture while a second bed is being evacuated. Before reaching the capacity of the gaseous mixture-supplied bed to adsorb the adsorbable component, the beds are brought toward pressure equilibrium by allowing the gas to flow (i.e., to be in fluid communication) between the beds. While gas is flowing between the beds, the supply of the gaseous mixture and the evacuation of the beds are reversed. That is, the gaseous mixture is supplied to the heretofore evacuated bed and the heretofore gaseous mixture-supplied bed is evacuated. Subsequent to reversing the supply of the gaseous mixture and the evacuation of the beds, the pressure equalization flow is terminated. These steps are cyclically repeated to provide continuing production of the nonadsorbable component.

The invention further encompasses a novel method of controlling the purge flow between the first and second sieve beds, particularly to optimize the relative time of flow between the beds. This new control method achieves a higher throughput efficiency to the patient, maximizes bed efficiency, and further facilitates remote control of the oxygen concentrator. When the microprocessor has the ability to compare the relative flow efficiencies of the sieve beds, it reduces the need for a technician to immediately visit and attend to the oxygen concentrator, for example when a device signals an alarm condition.

It is a further advantage of the invention to provide a software-driven microcontroller which continuously checks the performance of the oxygen concentrator assuring proper operation and warning of pressure extremes. An additional advantage of the invention is the provision of pressure-based software logic which compensates for compressor efficiency assuring high oxygen concentrations at higher elevations as well as for aging compressor maturity.

In accordance with another aspect of the present invention, there is also provided an apparatus for physically separating molecules of oxygen from a gaseous mixture. The apparatus comprises first and second beds each containing a physical separation material. A cross-over valving means selectively connects an inlet of one of the first and second beds with a supply of the gaseous mixture under pressure and an inlet of the other bed with a vacuum source. A control means causes the cross-over valving means to connect each of the first and second beds cyclically with the gaseous mixture supply, i.e., compressor, and to be vented for evacuation to atmosphere. The period of time in which one of the beds goes through a cycle of being connected with the gaseous mixture supply and being evacuated is denoted as a cycle duration. Alternatively, it is possible to regulate the production cycle based on the output pressure from the beds as measured by pressure transducers in the outlet flow path. A flow path which connects outlets of the first and second beds has a gas flow capacity which is sufficient to bring the first and second beds into substantial correspondence in oxygen output.

A concentration equalization valve which selectively permits and prevents gas flow through the flow path is in communication with the control means. The control means causes the concentration equalization valve to open for a portion of the cycle duration before each actuation of the cross-over valving means and to be closed for a portion of the cycle duration after each actuation of the cross-over valving means. A reservoir or product tank is operatively connected with the first and second bed outlets by unidirectional valving means to collect oxygen molecules which have been separated by the first and second beds. The control means utilizes a feedback loop to evaluate the concentration equalization valve flow setting (i.e., time to achieve optimal evacuation) between the two beds. As used herein, "feedback loop" refers to a circuit which operates on a variable and then compares that variable to its previous value in order to perform a function, in this case to evaluate the time setting of the concentration equalization (CE) valve based on oxygen concentration.

An additional aspect of the invention relates to the use of a control system which utilizes a variable pressure-based control to drive the cross-over valve and switch the cycling relative to the first and second molecular sieve beds. Specifically, the control will readjust the sieve bed pressure in order that the residence time of the fractionation gases stay within a certain defined range. Thus, for example, if a given sieve bed size and packing arrangement requires a minimum diffusion time, the controller will readjust the pressure to compensate such as for a higher flow rate which a higher-power compressor might provide. Thus, the circuit applies logic utilizing pressure and time parameters to define the product cycle duration. Likewise, oxygen concentration at the bed output can be utilized to define the product cycle duration.

A primary advantage of the present invention is that it provides relatively high primary product production capacity.

Another advantage of the present invention is that it produces oxygen at a sufficiently high flow rate and purity for medical applications and for providing oxygen-enriched breathing air for patients.

Another advantage of the present invention is that the additional control functions are delegated to an improved microprocessor to reduce the need for field servicing by a technician.

DETAILED DESCRIPTION OF THE PREFERRED EMBODIMENT

Figure 1:
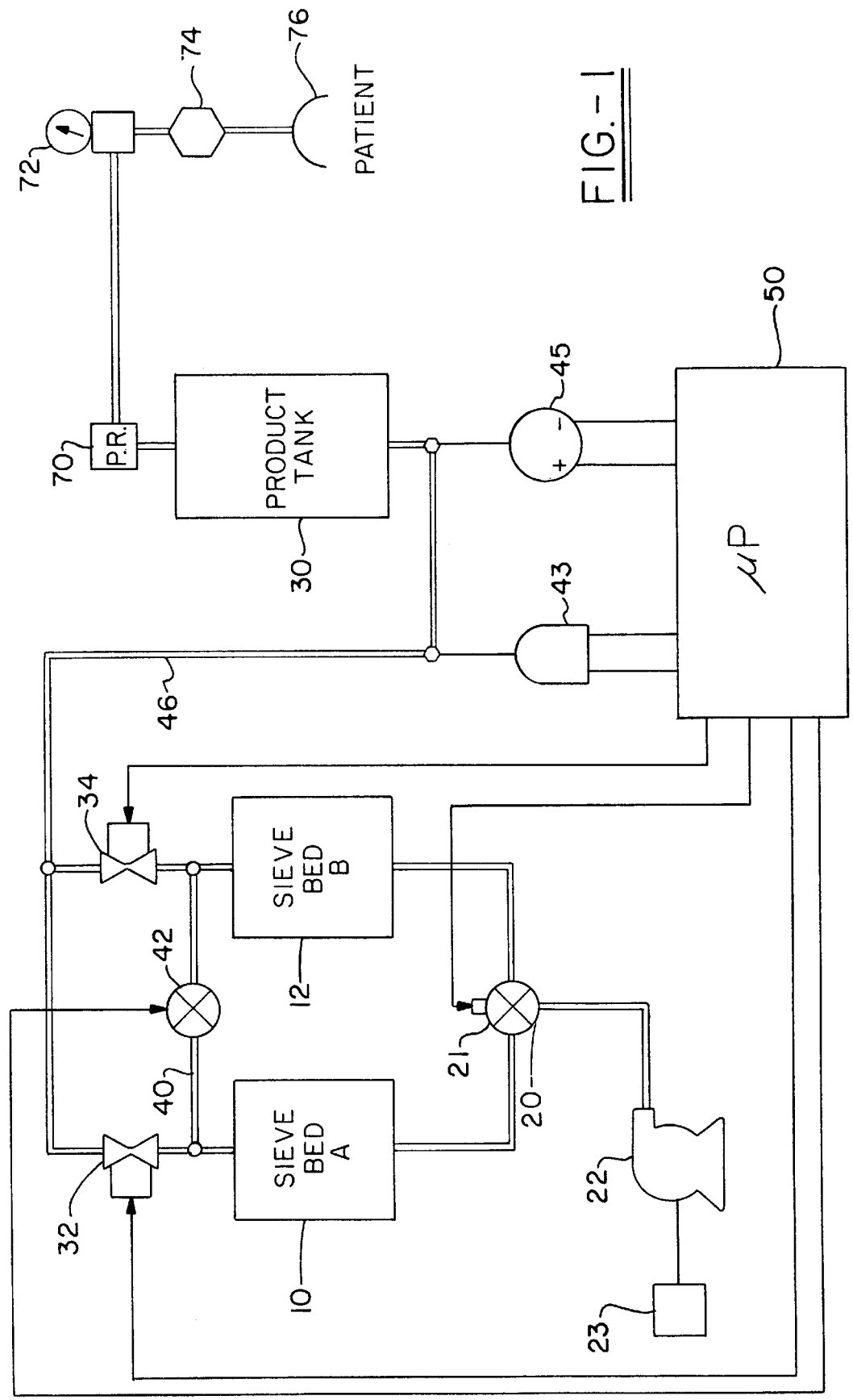
FIG. 1 is a block diagram of an apparatus in accordance with the present invention for separating a primary product gas from a gaseous mixture.

With reference to FIG. 1, the apparatus includes at least two beds 10 and 12 which are filled with a physical separation medium or material. The separation material selectively adsorbs one or more adsorbable components and passes one or more nonadsorbable components of such a gaseous mixture. The physical separation material is a molecular sieve with pores of uniform size and essentially the same molecular dimensions. These pores selectively adsorb molecules in accordance with molecular shape, polarity, degree of saturation, and the like. In the preferred embodiment, the physical separation medium is an aluminasilicate composition with 4 to 5 Å (Angstrom) pores. More specifically, the molecular sieve is a sodium or calcium form of aluminasilicate, such as type 5A zeolite. Alternately, the aluminasilicate may have a higher silicon-to-aluminum ratio, larger pores, and an affinity for polar molecules, e.g., type $13x$ zeolite. The zeolite adsorbs nitrogen, carbon monoxide, carbon dioxide, water vapor, and other significant components of air.

A cross-over valving means 20, which preferably includes a four-way valve 21, selectively and cyclically connects the inlet end of two beds, one at a time, during a production phase with a source of the gas mixture, e.g., air under pressure supplied from a compressor 22, while the other bed is vented to atmosphere during a purge phase. Specific to the preferred embodiment, the cross-over valving means selectively connects one of the beds in fluid communication with an air pump or compressor 22 which supplies air under about 15–30 pounds per square inch. As used herein, "fluid communication" refers to means allowing flow of the appropriate gases. Of course, vacuum can also be used during the purge phase with the present invention to enhance evacuation. The compressor is connected to a drive motor 23, in the preferred embodiment about a ¼-horsepower electric motor. A solenoid (not shown) or other cross-over valve actuating means selectively causes the cross-over valving means to move alternately between first and second positions. In the first position, illustrated in FIG. 1, the first bed 10 is connected with the compressor 22 to cause nitrogen adsorption and oxygen enrichment in the product gas, and the second bed 12 is vented to atmosphere to allow evacuation. In the second position, the first bed is vented to atmosphere to allow evacuation and the second bed is connected with the air compressor to cause nitrogen adsorption.

As the gas mixture is introduced through a bed inlet to an adsorbed, gas-free or regenerated bed, an adsorption zone of finite, relatively large size is formed. This adsorption zone is a region of the bed in which the full capacity of the adsorbent to hold the adsorbable components has not been reached. The composition of the gas in the voids of the zeolite varies from substantially pure primary-product gas at the outlet end, to the ambient gaseous mixture composition at the inlet end. This adsorption zone moves from the bed inlet toward a bed outlet with a velocity significantly less than the superficial gas velocity in the bed. When the adsorption zone reaches the outlet end of the bed, adsorbable components begin to flow through the bed outlet into the nonadsorbable primary product stream. This time is hereinafter referred to as the "breakthrough." For a given gaseous composition, the breakthrough is defined by the size and configuration of the bed container as well as the packing configuration of the molecular sieve and the flow rate and bed gas pressure. The configuration is generally cylindrical, while the output volume rate can vary from about 0 to 6 liters per minute, and more specifically 3, 5, and 6 liters, respectively. The breakthrough is the time required for the diffusion reaction as the nitrogen saturates and is weakly bonded to the sieve bed. When breakthrough occurs, primary product-enriched bed gas in the zeolite voids varies from a higher primary product gas concentration at the bed outlet to a lower concentration at the bed inlet. In the preferred embodiment, the primary product-enriched bed gas is about 80 percent primary product at breakthrough. While adsorption is occurring in one bed, the adsorbable components adsorbed by the separation medium of the other bed are purged from the other bed because of the drop in pressure due to atmospheric venting and because of exposure to relatively pure product gas from the first tank.

The first bed 10 is connected with a reservoir or product tank 30 by way of a first check valve 32 or other unidirectional valving means. The first check valve 32 permits the primary product gas from the first bed 10 to flow into the reservoir or product tank 30 when product gas pressure in the first bed 10 exceeds the pressure of product gas in the reservoir or product tank 30. The first check valve prohibits the product gas from flowing from the reservoir or product tank 30 when the pressure in the first bed 10 is lower than the reservoir or product tank. More specific to the preferred embodiment, the check valve imposes a 1.5 psi bias such that flow is only permitted when the pressure in the first bed exceeds the pressure in the reservoir or product tank by 1.5 psi. The second bed 12 is connected with the reservoir or product tank 30 by way of a second check valve 34 or other unidirectional valving means. The second check valve 34 again provides for unidirectional flow of the primary product gas through product conduit 46 from the second bed 12 to the reservoir or product tank 30.

A pressure equalization flow path 40 extends between outlets of the first and second beds. A concentration equalization valve 42 is either open or closed to selectively permit or prevent gas flow through the flow path between the first and second beds. A control means 50 cyclically causes the cross-over valve actuating means (i.e., two solenoids) and the concentration equalization valve 42 to be operated. The control means periodically and cyclically enables a concentration equalization valve actuator which is also a solenoid.

Oxygen sensor 43 registers the oxygen concentration of the product gas and can be located in the product tank 30. The sensor 43 communicates a sensed value to the microprocessor (i.e., control means). Similarly, a pressure sensor 45 registers the pressure in the product tank and communicates the same to the microprocessor.

The control means causes the cross-over valving means 20 to alternate between its first and second positions for the appropriate period during each cycle segment. A cycle segment can be either the product gas generation cycle or the purge cycle. The cycle duration is selected such that each bed is connected with the source of air for a duration which is equal to or less than the breakthrough time. The mechanism which triggers the cross-over valving can be based on the pressure, such as a pressure set point or set point range, in the bleed line from the product tank as is used in a pressure-based control cycle, or it can be based strictly on a residence time from the product-producing bed, such as in a timing cycle-based control cycle. In accordance with another embodiment of the invention, the control cycle can utilize variable pressure in order to achieve a residence time within a defined range based upon a projected breakthrough time. In the preferred embodiment, the beds are 3.5 inches in diameter, 15 inches in length, and each contains 6.5 pounds of 5A zeolite.

The gas mixture is supplied up to 32 pounds of pressure to the first bed. Concurrently, the second bed (i.e., a "used" bed) is vented to atmosphere to cause purging of the nitrogen-enriched molecular sieves. Before the breakthrough time, the concentration equalization valve is opened allowing primary product-enriched gas from the first bed to flow into the evacuated second bed. During the concentration equalization period, one bed is evacuated and the other has just reached the pressure set point which drives flow between the beds. The flow is of high oxygen content so that the first product to pass into the product tank is essentially product gas produced by the oxygen beds. The second bed pressure is product-enriched gas to purge the sieve bed. Before the primary product-enriched gas from the first bed is evacuated through the second bed, the cross-over valving means 20 is actuated to reverse its position. Actuating the cross-over valving means discontinues supplying of the gaseous mixture to the first bed and commences evacuating it and concurrently discontinues evacuating the second bed and commences supplying it with the gaseous mixture.

Subsequent to the actuation of the cross-over valving means, the concentration equalization valve 42 remains open to continue allowing a purge supply of product-enriched gas to flow into the second bed. This equalizes the concentration of gas which is supplied to the product tank since the cycling is sequenced so that the product gas proceeds the breakthrough zone to flow into the product tank. Subsequently, the concentration equalization valve closes and terminates the flow of primary-product gas between the beds. In the second segment of the cycle, the pressure in the second bed increases approaching the 32 psi gas mixture source pressure. Concurrently, the pressure in the first bed decreases approaching atmospheric pressure. Before the secondary product molecules have traversed the second bed, the concentration equalization valve 42 is opened allowing the primary product-enriched gas in the zeolite voids of the second bed to flow to the first bed. While the primary product-enriched gas is flowing to the first bed, the cross-over valving means is actuated. Actuating the cross-over valving means discontinues the evacuation of the first bed and commences supplying the gaseous mixture and concurrently discontinues supplying the gaseous mixture to the second bed and commences evacuating it. Subsequent to actuating the cross-over valving means, the concentration equalization valve is closed terminating the pressure equalizing flow of the primary product-enriched gas between the beds. The steps are cyclically repeated to provide continuing fractionating of the primary product gas from the mixture.

Figure 2:
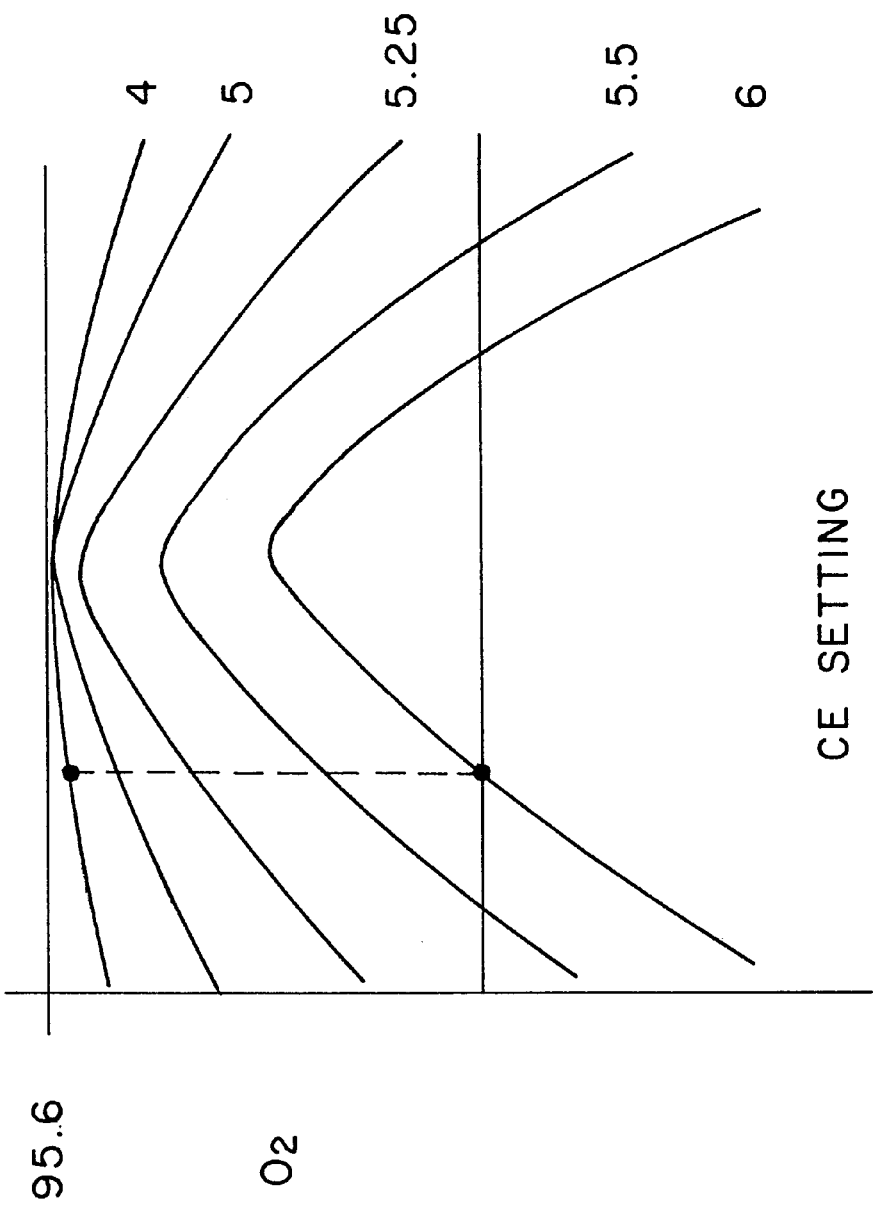
FIG. 2 illustrates oxygen production capacity as a function of concentration equalization setting valve operation time for the apparatus of FIG. 1.

In accordance with the invention, the time that the concentration equalization valve remains open (in one direction) and, consequently, the amount of primary-product gas which is allowed to flow into the bed which is being evacuated is controlled by the microprocessor to optimize (maximize) the oxygen outflow to the patient. FIG. 2 illustrates the oxygen concentration of the product gas as it varies with the concentration equalization valve setting. The setting is shown as achieving an optimal oxygen concentration output at a concentration equalization valve setting.

Figure 3:
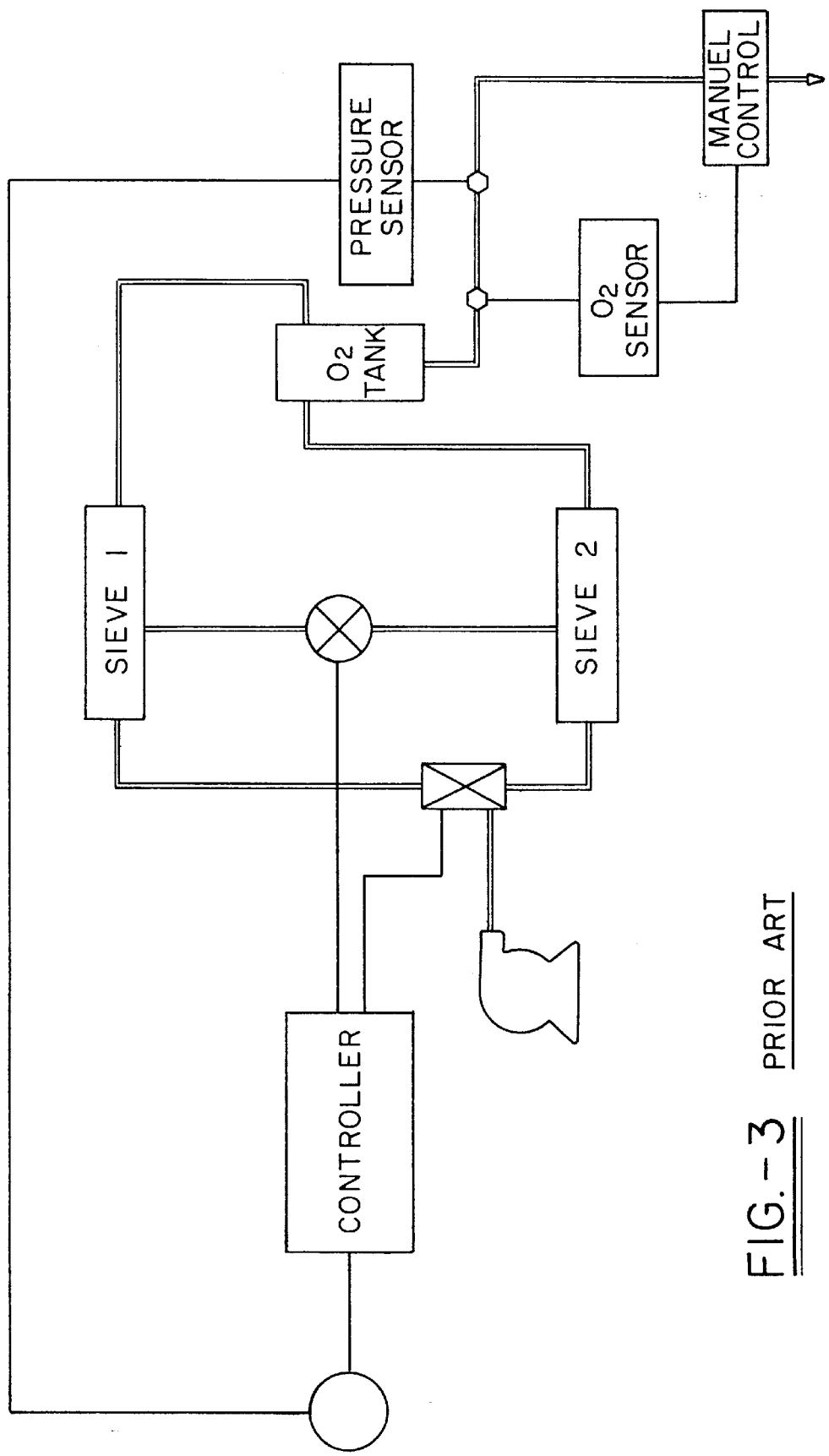
FIG. 3 is a schematic of the control for the prior art.
Figure 4:
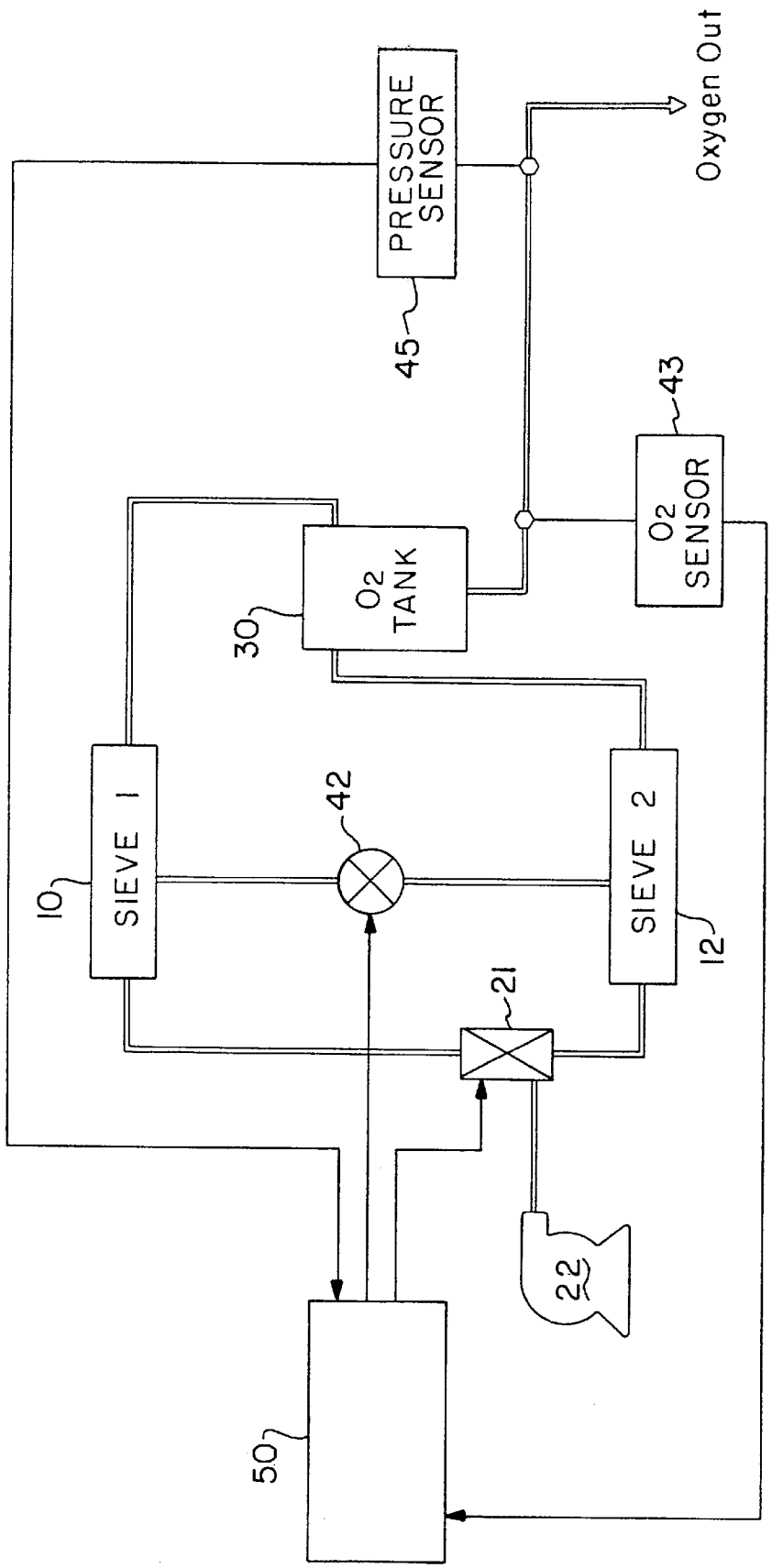
FIG. 4 is a schematic of the control for the present application.

FIGS. 3 and 4 are schematic representations of the control scheme for an oxygen concentrator wherein FIG. 3 illustrates the prior art, and FIG. 4 represents the present invention.

In particular, the concentration equalization flow valve starts at an initial setting, and after a first waiting period which happens to be from about 1 minute to 1 hour, preferably from 2 minutes to 30 minutes, and more preferably from 5 to 12 minutes, the microprocessor will cause a concentration equalization flow valve adjustment means to change one time unit increment. Each time unit increment is from about 1 to about 50 milliseconds, more preferably about 10 to 30 milliseconds. After an additional incremental waiting period, i.e., a second 10-minute period, the closed-loop feedback circuit compares a voltage value from the oxygen corresponding to oxygen output to the last determined value immediately prior to the incremental time unit change. If the value increases, the microprocessor causes the concentration equalization valve adjustment means to change an additional time unit increment in the same direction (i.e., directing a longer or shorter flow of output gas into the purging bed). The microprocessor will continue this process of incremental time unit adjustment and comparison of the oxygen outflow in the same direction until the circuit senses a drop in the value at which point the circuit will direct the time unit adjustment means to step back one unit to the last optimized setting. This sequence is illustrated in FIG. 4 which is a flow chart of the control circuit.

Referring again to FIG. 1, in the preferred embodiment the reservoir or product tank 30 maintains a reservoir of oxygen at a minimum pressure of about 18 psi. The reservoir or product tank is connected with a pressure regulator 70 for controlling the pressure or flow rate of oxygen to the patient. A flow meter 72 provides a visual indication of the rate at which the patient is receiving oxygen. A humidifier 74 adds moisture to the oxygen primary product to replace the moisture removed by the beds. A breathing apparatus 76 assists in delivering the oxygen to the patient. Most medical prescriptions require that oxygen be supplied to the patient at the rate of 6 liters per minute or less.

While in accordance with the patent statutes the best mode and preferred embodiment has been set forth, the scope of the invention is not limited thereto, but rather by the scope of the attached claims.

What is claimed is:

1. A method of fractionating a first-component gas from a second-component gas, in a gas concentrator having at least two fractionation beds having an inlet end and spaced from an output end, said beds each in selective fluid communication with the other bed at the output end by a concentration equalization flow path, the flow of gas in said concentration equalization flow path being regulated by a concentration equalization valve having a plurality of incremental concentration equalization settings and electronic control means having memory means operatively communicating with said concentration equalization valve and sensor means to determine a first-component gas output, said method comprising the steps of using said electronic control means to determine a first value by measuring the first-component gas output of at least one of said two fractionation beds, and storing said first value in said memory; using said electronic control means to change said concentration equalization valve by at least one incremental concentration equalization setting to a second valve setting;

using said electronic control means to determine a second value by measuring the first-component gas output of said at least one fractionation bed with said concentration equalization valve at said second valve setting and using said electronic control means to store said second value in said memory and compare said first and second values to evaluate concentration equalization setting and said electronic control means operatively changing the concentration equalization setting to maximize said first-component gas output.

2. A method of fractionating gases according to claim 1, wherein the first and second values represent the output of the first-component gas of the first and second fractionation beds together.

3. A method of fractionating gases according to claim 2, wherein said electronic control means is a microprocessor which is integral to the gas concentrator.

4. A method of fractionating gases according to claim 2, wherein the method is repeated periodically.

5. A method of fractionating gases according to claim 4, wherein there is a delay of from about 0.1 to about 10 minutes between the determination of the first value and the second value, and there is a period of from about 0.001 to about 2 seconds between the concentration equalization valve setting.

6. A method of fractionating gases according to claim 5, wherein said delay is from about 1 to about 5 minutes between the determination of the first value and the second value, and said period is from about 0.001 to about 1 seconds between the concentration equalization valve setting.

7. A method as set forth in claim 1, wherein said electronic control means is remote from said gas concentrator.

8. A method as set forth in claim 7, wherein said electronic control means is in telephone communication with said gas concentrator.

9. A method as set forth in claim 1, wherein the concentration valve setting is incrementally changed to alter the time of fluid communication from the first bed to the second bed while the time of fluid communication from the second bed to the first bed remains the same.

10. A method as set forth in claim 9, wherein the increment of time change of fluid communication is from about 1 to 50 milliseconds.

11. A method as set forth in claim 1, wherein said concentration equalization valve incremental settings relate to the period of time that output gas from the second bed flows through the concentration equalization flow path relative to the amount of time that the output gas flow from the first bed through the concentration equalization flow path.

12. A method as set forth in claim 11, wherein said incremental settings increase the amount of time that the gas flows from the second fractionation bed through the concentration equalization flow path while the amount of time that the gas flows from the first fractionation bed through the concentration equalization flow path is held constant.

13. A method as set forth in claim 12, wherein said settings represent increments in the time of 1 to 40 milliseconds.

14. A method of fractionating a first-component gas from a second-component gas in a gas concentrator having at least two gas fractionation beds having an input end spaced by an area containing fractionation media from an output end, said beds each in first selective fluid communication with a pressurized gas supply source and alternatively with a depressurization source in second selective fluid communication with the other at the output end by a concentration equalization flow path, said first selective fluid communication being regulated by a cross-over valve, and electronic control means having memory means operatively communicating with said cross-over valve to comprise a pressurization cycle control, said method comprising defining a residence time range during which gas from said pressurized gas supply source is in contact with said fractionation media and said electronic control means regulating said first fluid communication on the basis of both the pressure sensed in said concentration equalization flow path and said residence time range whereby said pressurization cycle control is a variable pressure cycle control.

15. A method as set forth in claim 14, wherein said second selective fluid communication is regulated by a concentration equalization valve which communicates with and is regulated by said electronic control means, said selective fluid communication being regulated by a concentration equalization valve.

16. A method of fractionating oxygen-enriched air from air in an oxygen concentrator having at least a first and a second oxygen fractionation bed each having an inlet end and spaced from an output end, said first oxygen fractionation bed in selective fluid communication with said second oxygen fractionation bed at the output end by a concentration equalization flow path, the flow of oxygen in said concentration equalization flow path being regulated by a concentration equalization valve having incremental settings and electronic control means having memory means operatively communicating with said concentration equalization valve and sensor means to determine oxygen concentration, said method comprising the steps of using said electronic control means to determine a first value by measuring the oxygen concentration of at least said first fractionation bed, and storing said first value in said memory; using said electronic control means to change said concentration equalization valve by at least one incremental setting to a second valve setting; using said electronic control means to determine a second value by measuring the oxygen concentration of said first fractionation bed with said concentration equalization valve at said second valve setting and using said electronic control means to store said second value in said memory and compare said first and second values to evaluate concentration equalization setting and said electronic control means operatively changing the concentration equalization setting to maximize the fractionation of oxygen.

17. A method of fractionating gases according to claim 16, wherein the first and second values represent the oxygen concentration of the first and second fractionation beds together.

18. A method of fractionating gases according to claim 17, wherein said electronic control means is a microprocessor which is integral to the oxygen concentrator.

19. A method of fractionating gases according to claim 18, wherein the method is repeated periodically.

20. A method of fractionating gases according to claim 19 wherein there is a delay of from about 0.1 to about 10 minutes between the determination of the first value and the second value, and there is a period of from about 0.001 to about 2 seconds between the concentration equalization valve setting.

21. A gas concentrator device for fractionating a first-component gas from a second-component gas comprising at least two fractionation beds in fluid communication with each other at the output end by a concentration equalization flow path, the flow of gas in said concentration equalization flow path being regulated by a concentration equalization valve having incremental settings, and electronic control means having memory means and a means to compare relative values, and measuring means to determine the output of said first gas component from a first one of said fractionation beds, whereby said electronic control means communicates with said measuring means to determine a first value by measuring the first-component gas output of said first fractionation bed and storing said first value in said memory means, said control means further changes said concentration equalization valve by at least one incremental setting and determines a second value by measuring the first-component gas output of said first fractionation bed and stores said second value in said memory, said electronic control means further comparing said first and second values and changing the incremental setting of said concentration equalization valve accordingly.

22. A device as set forth in claim 21 said electronic control means comprises a microprocessor in communication with a solenoid which operates upon said concentration equalization valve.

23. A device as set forth in claim 22, wherein said measuring means comprises at least one of an oxygen concentration sensor and a pressure transducer.

24. A gas concentrator device for fractionating a first-component gas from a second-component gas comprising at least two fractionation beds in fluid communication with each other at the output end by a concentration equalization flow path, the flow of gas in said concentration equalization flow path being regulated by a concentration equalization valve having incremental settings, and a microprocessor having a memory and a comparator, and a sensor to determine the output of said first gas component from a first one of said fractionation beds, whereby said microprocessor communicates with said sensor to determine a first value by measuring the first-component gas output of said first—fractionation bed and storing said first value in said memory, said microprocessor further changes said concentration equalization valve by at least one incremental setting and determines a second value by measuring the first-component gas output of said first fractionation bed and stores said second value in said memory, said microprocessor further comparing said first and second values and changing the incremental setting of said concentration equalization valve accordingly.

25. A gas concentrator as set forth in claim 24, wherein said microprocessor is remote from said gas concentrator.

\* \* \* \* \*